United States Patent [19]

Taub

[11] Patent Number: 5,714,027

[45] Date of Patent: Feb. 3, 1998

[54] METHOD OF FOLDING AND HANDLING A WEB OF MATERIAL IN A CONTINUOUS OPERATION

[75] Inventor: Stewart Lawrence Taub, West Chester, Ohio

[73] Assignee: The Procter & Gamble Company, Cincinnati, Ohio

[21] Appl. No.: 620,629

[22] Filed: Mar. 22, 1996

[51] Int. Cl.$^6$ .............................. A61F 13/15; A61F 13/60
[52] U.S. Cl. .................. 156/204; 156/201; 156/227; 156/463; 156/465; 604/386
[58] Field of Search ........................ 156/204, 201, 156/200, 461, 463, 465, 227; 604/386

[56] References Cited

U.S. PATENT DOCUMENTS

| | | |
|---|---|---|
| 3,875,836 | 4/1975 | Hutchinson et al. |
| 3,875,837 | 4/1975 | Dussaud. |
| 4,614,512 | 9/1986 | Capdeboseq. |
| 4,760,764 | 8/1988 | De Jonckheere et al. |
| 4,811,641 | 3/1989 | Müller. |
| 4,862,574 | 9/1989 | Seidy. |
| 4,893,534 | 1/1990 | Köbler. |
| 5,110,386 | 5/1992 | Ochi et al. |
| 5,279,195 | 1/1994 | Breton. |
| 5,354,400 | 10/1994 | Lavash et al. |
| 5,389,094 | 2/1995 | Lavash et al. ............... 604/386 X |
| 5,453,143 | 9/1995 | Menard ........................ 156/204 |

FOREIGN PATENT DOCUMENTS

| | | |
|---|---|---|
| 0 539 032 A1 | 9/1992 | European Pat. Off. |
| 2 644 694 | 9/1990 | France. |
| 9427541 | 12/1994 | WIPO ........................ 604/386 |

*Primary Examiner*—Jeff H. Aftergut
*Attorney, Agent, or Firm*—Edward J. Milbrada; Jeffrey V. Bamber; Steven W. Miller

[57] ABSTRACT

A method of folding and handling a web of material in a continuous manufacturing operation is disclosed. The method can be used during the process of making disposable absorbent articles, such as sanitary napkins and the like which have side flaps. During the method, a discontinuous portion (or tab) defined by the distal edge of the web of flap material is held stationary and the continuous portion (or continuous ribbon) of the web of flap material is folded.

2 Claims, 6 Drawing Sheets

METHOD OF FOLDING AND HANDLING A WEB OF MATERIAL IN A CONTINUOUS OPERATION

FIELD OF THE INVENTION

This invention relates to methods of folding and handling a web of material in a continuous manufacturing operation. More particularly, the invention relates to a method of folding and handling a web of material during the process of making disposable absorbent articles.

BACKGROUND OF THE INVENTION

All manner and variety of absorbent articles configured for the absorption of body fluids such as menses, urine, and feces are, of course, well known. Absorbent articles, particularly sanitary napkins, having wings or flaps are disclosed in the literature and are available in the marketplace. Generally, the flaps of such sanitary napkins extend laterally from a central absorbent means and are intended to be folded around the edges of the wearer's panties in the crotch region.

Several preferred sanitary napkins having flaps are described in U.S. Pat. No. 4,589,876 entitled "Sanitary Napkin", which issued to Van Tilburg on May 20, 1986, U.S. Pat. No. 4,687,478, entitled "Shaped Sanitary Napkin With Flaps", which issued to Van Tilburg on Aug. 18, 1987, U.S. Pat. No. 5,389,094 entitled "Absorbent Article Having Flaps and Zones of Differential Extensibility", which issued to Lavash, et al. on Feb. 14, 1995, and U.S. Pat. No. 5,281,209 entitled "Absorbent Article Having Tucked Flaps", issued to Osborn, et al. on Jan. 25, 1994, describes a particularly preferred sanitary napkin having flaps that are folded and tucked into recessed portions.

In order to manufacture large quantities of sanitary napkins, or other absorbent articles having flaps, several complications arise. This is particularly the case when the flaps comprise separate components that are to be attached to the main body portion of the absorbent article. The manufacture of such absorbent articles is further complicated when the flaps are tucked as described in the aforementioned U.S. Pat. No. 5,281,209.

One of the challenges in the manufacture of disposable absorbent articles is that it is desirable to make the manufacturing process as economical as possible and to reduce the amount of waste material in such processes to a minimum since such article must be priced for disposability. The goal of reducing waste material is particularly challenging when manufacturing absorbent articles having flaps or other side extensions since the components of such absorbent articles are typically cut from continuous rectangular webs of material. A number of attempts have been made in an effort to solve this problem. However, these prior processes suffer from a number of drawbacks.

For example, EPO Publication No. 0 539 032 A1 published in the name of Brisebois, et al. on Apr. 28, 1993, is directed to a method of making a tabbed absorbent article that utilizes a nested cutting arrangement for the tab or flap material. The Brisebois publication shows one of the drawbacks of producing absorbent articles with tabs or flaps. The nested cutting of the web of flap material leaves the cut flaps on the wrong side of the web of absorbent article to which they need to be attached. This requires that the webs of flap material be crossed over to opposite sides of the web of absorbent article so that they can be joined to the proper side of the absorbent body. This can create numerous tracking and registration complications.

Prior techniques that would generally be used for folding the wings or flaps of such absorbent articles would employ one or more geometrically shaped elements often referred to as "folding boards" or "folding plows" that would gradually turn one portion of the continuous web of the material over another portion of the web to form the fold. The need to fold the webs of flap material would further complicate a process in which it was already necessary to cross the webs of flap material prior to attachment of the individual flaps to the main body portion of an absorbent article.

Therefore, it is an object of the present invention to provide a method for producing disposable absorbent articles having flaps with a minimum amount of waste.

It is an additional object of the present invention to provide a method for attaching flaps to an absorbent body that does not require any crossing over of webs of cut flaps material for joining the flap material to an absorbent body.

These and other objects of the present invention will be more readily apparent when considered in reference to the following description and when taken in conjunction with the accompanying drawings.

SUMMARY OF THE INVENTION

This invention relates to a method of folding and handling a web of material in a continuous manufacturing operation. More particularly, the invention relates to a method of folding and handling a web of a material during the process of making disposable absorbent articles, such as sanitary napkins and the like.

In a preferred embodiment of the method of the present invention, the web of material to be folded comprises a web of flap material that has a continuous portion along one edge and a discontinuous portion along the other edge. In this preferred embodiment of the method, the discontinuous portion of the web of flap material comprises a plurality of outwardly extending tabs or flaps and has cut out or recessed areas therebetween.

Generally, when conventional folding techniques are used to fold a web of material that comprises a continuous portion and a discontinuous portion, the folding process will maintain control of the continuous portion, and the folding plows will be used to fold the discontinuous portion. In contrast, in the particularly preferred embodiment of the method of the present invention, during at least one of the folding operations, the discontinuous portion (or tab) defined by the distal edge of the web of flap material is preferably held in position relative to the machine direction centerline and the continuous portion (or continuous ribbon) of the web of flap material is folded. The tab portion can be held in place by any suitable means, such as by vacuum conveyors while the continuous ribbon travels through the folding plow(s) in order to fold the web of flap material in the desired manner.

Therefore, the method of folding a web of material which has a continuous portion and a discontinuous portion of the present invention comprises the steps of:

(a) providing a web of material which has a continuous portion and a discontinuous portion;

(b) transporting said web of material in a machine direction wherein the web of material is generally centered from lateral displacement about a machine direction centerline;

(c) maintaining the discontinuous portion of said web of material in position relative to the machine direction centerline; and (d) folding the continuous portion of the web of material about the discontinuous portion.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

This invention relates to a method of folding and handling a web of material in a continuous manufacturing operation. More particularly, the invention relates to a method of folding and handling a web of a material during the process of making disposable absorbent articles, such as sanitary napkins and the like.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, incontinence pads, and diapers. The term "disposable" refers to articles which are intended to be discarded after a single use and preferably recycled, composted, or otherwise disposed of in an environmentally compatible manner. (That is, they are not intended to be laundered or otherwise restored or reused as an absorbent article.)

Figure 1:
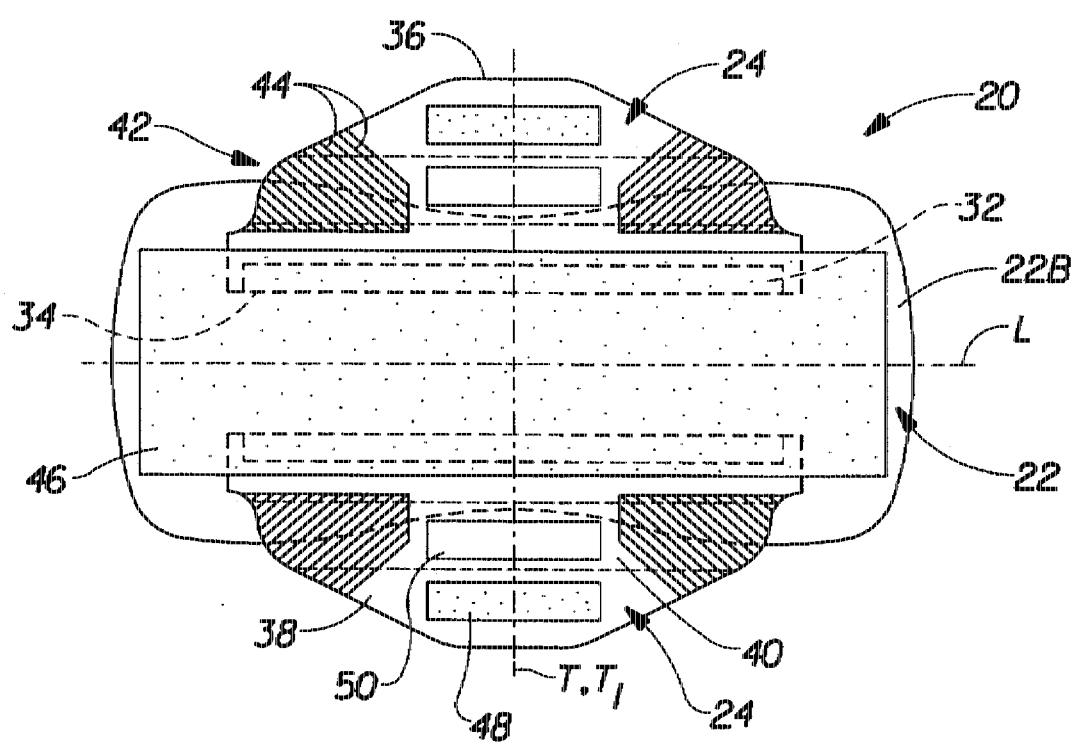
FIG. 1 is a bottom plan view of a sanitary napkin of a type that can be folded according to the method of the present invention, shown with its flaps extended.

A preferred embodiment of a sanitary napkin 20 made by the present invention is shown in FIG. 1. The term "sanitary napkin", as used herein, refers to an article which is worn by females adjacent to the pudendal region that is intended to absorb and contain the various exudates which are discharged from the body (e.g., blood, menses, and urine). The method of the present invention, however, is not limited to the production of the particular types or configurations of absorbent articles shown in the drawings. As shown in FIG. 1, the sanitary napkin 20 basically comprises an absorbent means represented by central absorbent pad (or "main body portion") 22, and two flaps 24.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

The main body portion 22 of the sanitary napkin 20 has two surfaces, a liquid pervious body-contacting surface or "body surface" 22A and a liquid impervious garment surface 22B. The sanitary napkin is shown in FIG. 1 as viewed from its garment surface 22B, and in FIG. 2 as viewed from its body surface. The body surface 22A is intended to be worn adjacent to the body of the wearer. The garment surface 22B of the main body portion 22 is intended to be placed adjacent to the wearer's undergarments when the sanitary napkin 20 is worn.

Figure 2:
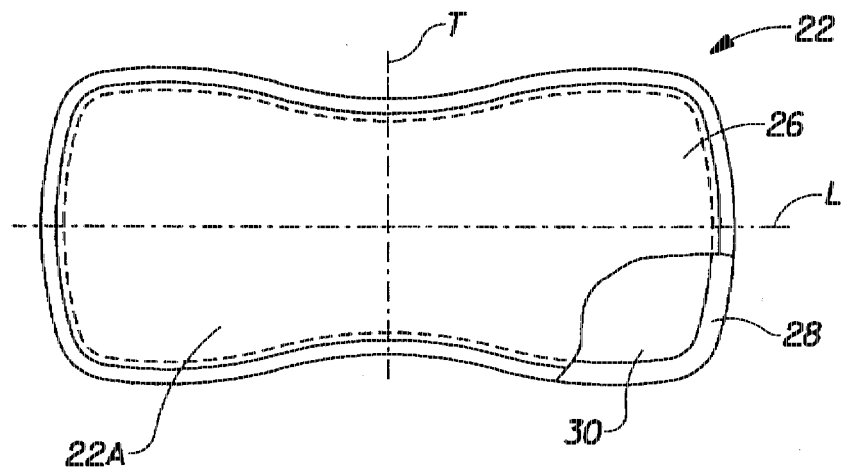
FIG. 2 is a schematic top plan view of the main body portion of the sanitary napkin shown in FIG. 1.

The main body portion 22 of the sanitary napkin 20, as shown in FIG. 2, is generally comprised of at least a topsheet 26, a backsheet 28, and an absorbent core 30. The topsheet, backsheet, and absorbent core can be comprised of any of the materials generally used for these particular purposes. Suitable materials for these components, and preferred arrangements for the assembly of the same, are described in greater detail in U.S. Pat. No. 5,389,094 entitled "Absorbent Article Having Flaps and Zones of Differential Extensibility", which issued to Lavash, et al. on Feb. 14, 1995, and U.S. Pat. No. 5,281,209 entitled "Absorbent Article Having Tucked Flaps", issued to Osborn, et al. on Jan. 25, 1994.

The flaps 24 are each associated with main body portion 22 along a juncture. This is typically a longitudinally-oriented (or "longitudinal") juncture, such as lines of juncture 32. As used herein, the terms "juncture" (or "line of juncture") refer to regions where the flaps 24 extend from, or are joined to, the main body portion 22. The flaps 24 can be integral with the main body portion 22, or with components of the main body portion, or they can comprise separate elements (i.e., pieces of material) that are joined to the main body portion 22. In the embodiment shown in FIG. 1, the flaps 24 are comprised of separate pieces of material which are joined to the main body portion 22. The separate flap pieces are preferably joined to the main body portion 22 by applying adhesive to the flap pieces in the region that will form the juncture 32.

The flaps 24 have a proximal edge 34 adjacent the line of juncture 32. A distal edge (or "free end") 36 is remote from the line of juncture 32. As shown in FIG. 1, each flap 24 is divided into a front half 38, and a back half 40 by a flap transverse centerline T1. Preferably, as shown in FIG. 1, the flaps 24 of the sanitary napkin 20 are provided with four zones of differential extensibility 42, one in the front half of each flap, and one in the back half of each flap. The term "zone of differential extensibility", as used herein, refers to a portion of the sanitary napkin 20 (in this case, a portion of the flap 24) which is capable of extending a differing amount (preferably a greater amount), than surrounding portions of the sanitary napkin 20. The zones of differential extensibility 42 relieve the stresses which develop in the flaps 24 when they are folded around a panty crotch. The zone(s) of differential extensibility 42 can comprise any structure capable of extending a greater amount than the surrounding portions of the sanitary napkin. Suitable structures for the zones of differential extensibility 42 are described in U.S. Pat. No. 5,389,094 issued to Lavash, et al. In the preferred embodiment shown in FIG. 1, the zones of differential extensibility 50 comprise regions of the flaps 24 that have been precorrugated or "ring rolled". The term "ring roll" refers to a process in which the material comprising the flaps is fed through intermeshing corrugated rolls.

The flaps 24 can be ring rolled in accordance with methods described in U.S. Pat. No. 4,107,364 issued to Sisson on Aug. 15, 1978, U.S. Pat. No. 4,834,741 issued to Sabee on May 30, 1989, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992. The ring rolling forms corrugations in the zones of differential extensibility 42. The corrugations are defined by fold lines or ridges and valleys 44. The fold lines 44 may form any angle desired relative to the principal longitudinal centerline L. In the preferred embodiment shown in FIG. 1, the fold lines 44 form an angle of between about 40°–45° with the principal longitudinal centerline L. This will provide the desired direction of extensibility.

FIG. 1 also shows the fasteners, such as adhesive attachment means, central pad adhesive 46 and flap adhesive 48, which are adapted to secure the sanitary napkin 20 to the crotch region of an undergarment. The central pad adhesive 46 provides an adhesive attachment means for securing main body portion 22 in the crotch portion of a panty. The garment-facing surface of flap 24 is preferably coated with a flap adhesive 48. The flap adhesive 48 can be positioned adjacent the distal edge 36 of the flap as shown. Alternatively, the positions of the flap adhesive and the unitary release material 50 (described below) can be reversed. The flap adhesive 48 is used to assist in maintaining the flap 24 in position after it is wrapped around the edge of the crotch portion of the wearer's panties. The flaps 24 can be maintained in position by attaching the flaps 24 to the undergarment, or to the opposing flap. Suitable adhesive fasteners are described in greater detail in U.S. Pat. No. 4,917,697.

The central pad adhesive 46 is preferably covered with a removable release liner to keep the central pad adhesive from sticking to extraneous surfaces prior to use. The flap adhesive 48 can also be covered with separate release liners. Preferably, however, the flaps 24 are provided with a unitary release material 50 that superposes the flap adhesive 48 when the flap 24 is folded along a fold line. Such an arrangement is described in U.S. patent application Ser. No. 08/402,769 filed in the name of Lavash, et al. on Mar. 13, 1995 (published as PCT Publication No. WO 94/00093 on Jan. 6, 1994). In a particularly preferred embodiment, after the flaps 24 are folded and tucked as described in U.S. Pat. No. 5,281,209, the central pad adhesive 46 is covered by a releasable wrapper that not only covers the central pad adhesive 46, but also serves as an individual package for the sanitary napkin. Suitable release liners that serve as an individual package for a sanitary napkin are described generally in U.S. Pat. No. 4,556,146 issued to Swanson, et al. and U.S. Pat. No. 5,462,166 issued to Minton, et al.

Figure 4:
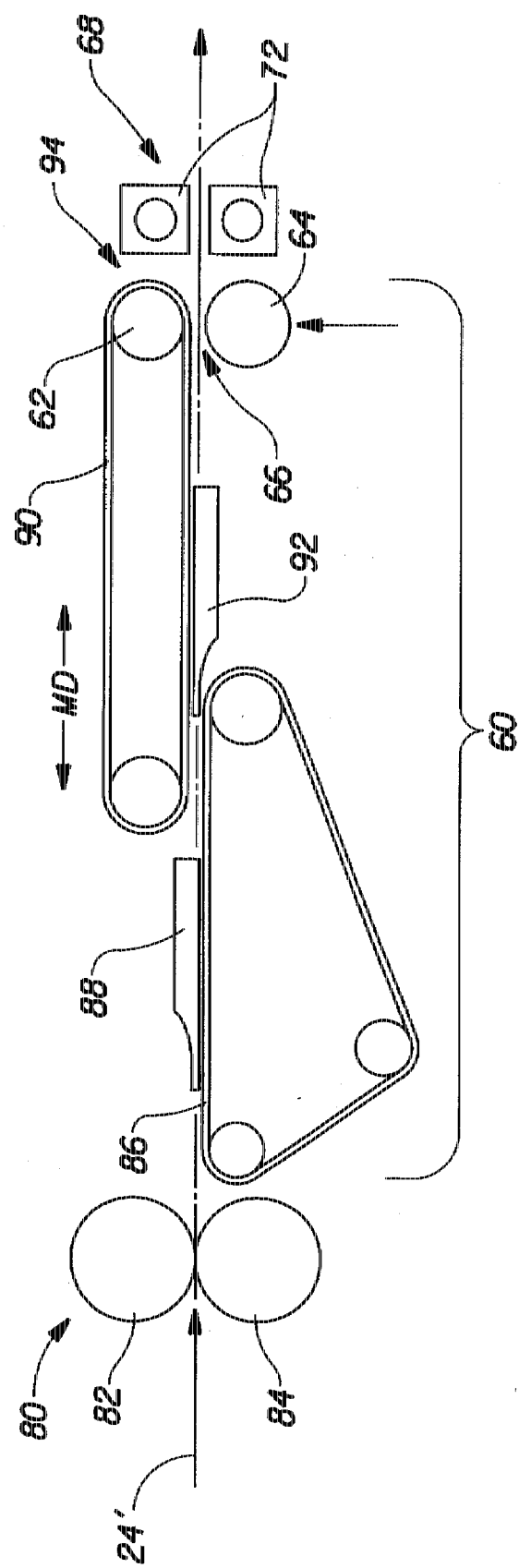
FIG. 4 is a schematic side view of a preferred embodiment of the method of folding the flap material of the present invention during the process of making the sanitary napkin shown in the preceding drawing figures.

FIG. 4 is a schematic side view of a preferred embodiment of the method and apparatus of folding and handling a web of material in a continuous operation of the present invention. The web of material in FIG. 4 preferably comprises a web of flap material 24' (although in other embodiments of the method, other types of materials can be folded). As shown in FIG. 4, the apparatus 60 comprises a cutting station 80, a first fold conveyor 86, a first folding plow 88, a second fold conveyor 90, a second folding plow 92, and a fold compression station 94.

Figure 3:
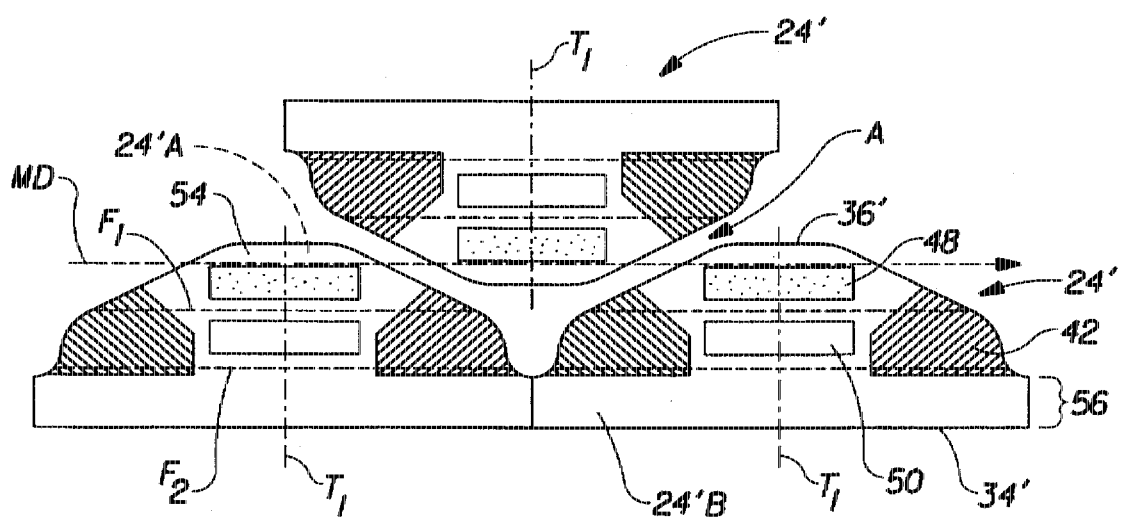
FIG. 3 is a plan view showing a step in the process of cutting the flaps for attachment to the sanitary napkin shown in FIG. 1.

In the preferred embodiment of the process of making the sanitary napkin 20 shown in the drawings, the flap material comes into the process in the form of a single continuous web of material. The flap material preferably comprises a laminate, at least one layer of which comprises a polyethylene film similar to that used as a backsheet material. Overlying the polyethylene film and bonded thereto to form the laminate is preferably a layer of nonwoven material or an apertured film suitable for use as a topsheet material. The single web of material is preferably cut along its length in a modified sine wave pattern as shown in FIG. 3 to form two continuous webs of flap material, one for each side of the sanitary napkin.

Several steps are preferably performed on this single web of material before it is cut into two continuous webs of flap material. It should be understood, however, that the steps described herein are used to form the preferred sanitary napkin shown in the drawings. All of the steps described herein may not be necessary when folding components for other, more simple types of absorbent articles, or other articles. It should also be understood that the order of many of the steps described herein can be varied (at least to a certain extent) if desired. In a preferred embodiment of the process, the single web of material is preferably ring rolled before any of the stages of the folding process.

The folding process begins with the forming of pre-formed folding lines, a first (or outer) pre-formed folding line $F_1$ and a second (or inner) pre-formed line $F_2$ in the single web of flap material. The pre-formed folding lines $F_1$ and $F_2$ are shown best in FIG. 3. The outer pre-formed folding line $F_1$ is closest to the portion of the web of flap material that will form the distal edge 36' of the flaps, after cutting the single continuous web into individual webs 24'. The pre-formed folding lines can be formed in any suitable manner known in the art. Preferably, the pre-formed folding lines are formed by forming a groove into (that is, by scoring) the web of flap material. A score line is formed in each place where the cut webs of flap material will be folded. The pre-formed fold lines $F_1$ and $F_2$ are preferably formed by scoring the garment-facing surface 24'B of the web of flap material.

The patches of flap adhesive 48 and unitary release material 50 are then preferably applied to the continuous web of flap material. The unitary release material 50 can comprise any suitable material that will releasably adhere to and cover the flap adhesive 48. Preferably, the unitary release material comprises a silicone coating. The single continuous web of flap material then moves on to the cutting station 80.

The cutting station 80 serves to cut the single continuous web of flap material into two continuous webs 24' that will form flaps for each side of the absorbent article. The cutting station shown in FIG. 4 preferably comprises a pair of metal rolls 82 and 84. One of the rolls is provided with a knife blade thereon that is configured to cut the webs in the area, A, shown in FIG. 3. As shown in FIG. 3, the continuous web of flap material is preferably cut so that there is a relatively small amount of waste material removed from between the cut webs of flap material 24'. Some material, however, is preferably removed between the webs of flap material 24' to obtain flaps of the preferred shape (that is, the webs 24' need not be in a fully nested arrangement, and preferably are not fully nested). During the cutting operation, and throughout the process described herein, the webs of flap material 24' move continuously in a machine direction, and are centered relative to a machine direction centerline (MD). The machine direction is the direction of movement of the web of flap material 24'. The movement of a web of main body portions for the sanitary napkin will also typically be moving in the machine direction, and the webs of flap material 24' will be cut into individual flaps and joined to a main body portion in a continuous operation.

As shown in FIG. 3, the webs of flap material 24' have been cut so that the distal edge 36' of each web defines a discontinuous portion 54 (that is, the distal edge 36' has areas cut out thereof, and is not linear). The proximal edge 34' of each web of flap material 24', on the other hand, defines a continuous ribbon portion 56. Generally, when conventional folding techniques are used to fold a web of material that comprises a continuous portion and a discontinuous portion, the folding process will maintain control of the continuous portion, and the folding plows will be used to fold the discontinuous portion. In contrast, as described in greater detail below, during at least one stage of the folding operation in the method of the present invention, the control of the web of flap material is accomplished by maintaining control of the discontinuous portion 54 of the web.

The webs of flap material 24' in the particular embodiment of the method of the present invention shown in FIG. 4 will each be folded twice. One fold, preferably the first fold, will position the flap adhesive 48 and the unitary release material 50 in an overlying relationship. Another fold, preferably the second fold, will fold the flaps so that they will be in a tucked position when they are attached to the main body portion 22 of the sanitary napkin 20. In other embodiments of the process, the webs of flap material may be folded only once, or more than twice.

Figure 5:
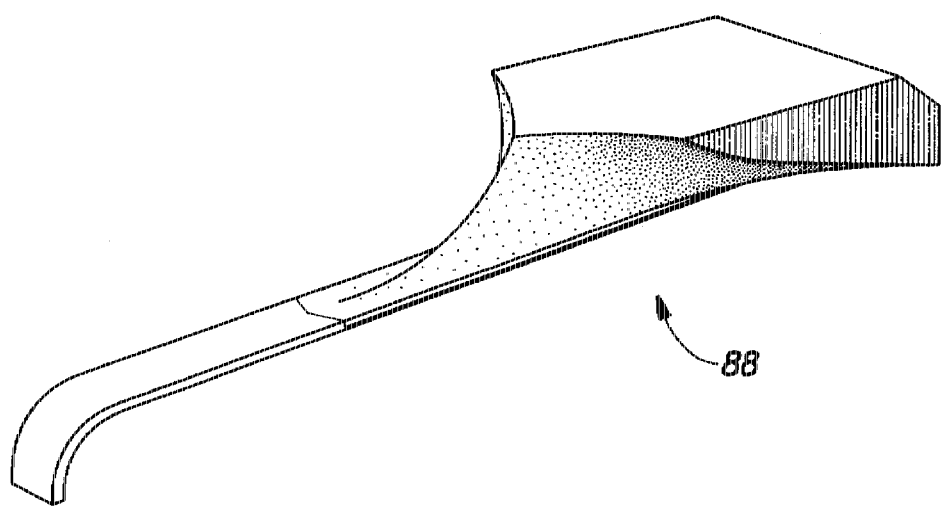
FIG. 5 is a perspective view of one of the folding plows used in the method of the present invention.
Figure 6:
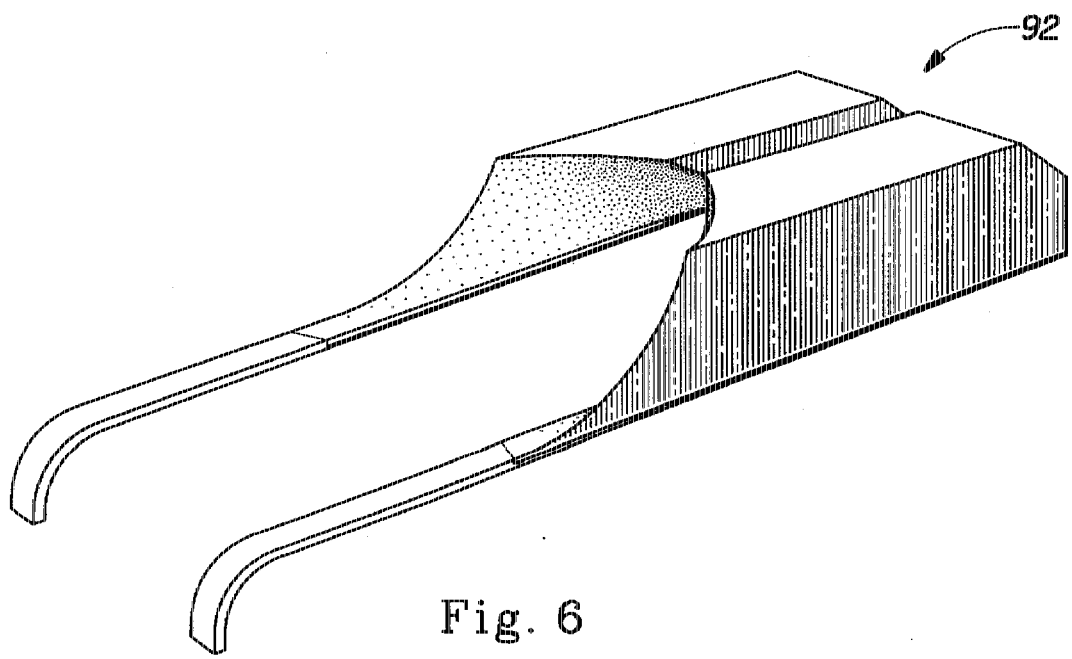
FIG. 6 is a perspective view of the other folding plow used in the method of the present invention (shown inverted from its orientation in FIG. 5 for clarity of illustration).

The webs of flap material 24' now pass through the folding apparatus 60. The folding apparatus 60 preferably comprises fold conveyors, such as a first fold conveyor 86 and a second fold conveyor 90, and a pair of folding plows such as first folding plow 88 and second folding plow 92. The pair of folding plows 88 and 92 will be used to sequentially form the two folds in both of the webs of flap material 24'. The folding plows 88 and 92 are provided in a configuration suitable for forming the particular folds in the webs of flap material 24'. The first folding plow 88 is shown in greater detail in FIG. 5. The second folding plow 92 is shown in greater detail in FIG. 6. The entire surface of each of the folding plows that will be contacted by the webs of flap material 24' are preferably hard coat annodized with Teflon impregnate according to techniques well known in the art.

Figure 6A:
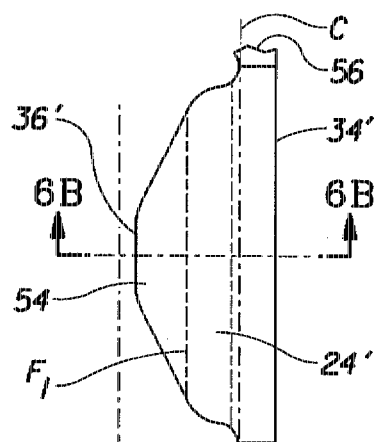
FIG. 6A is a top plan view of a section of a continuous web of flap material before folding.
Figure 6B:
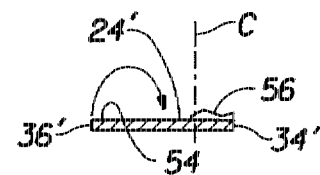
FIG. 6B is a cross-sectional view of the web of material shown in FIG. 6A taken along line 6B—6B of FIG. 6A.

The sequence of folds formed by the process of the present invention is shown in FIGS. 6A–8B. FIGS. 6A and 6B show the position of one of the webs of flap material 24' relative to the machine direction centerline, MD, prior to folding the same. FIGS. 6A and 6B also show the position of one of the webs of flap material 24' relative to a folding centerline, C. There will be a folding centerline, C, for each of the webs of flap material 24'. The folding centerline C divides the discontinuous portion 54 and the continuous ribbon portion 56 of the web of flap material 24'. The other web of flap material 24', which is not shown in FIGS. 6A and 6B, will be on the other side of the machine direction centerline MD with its distal edge 36' facing the web of flap material shown.

As shown in FIGS. 6A and 6B, at this stage of the process, the web of flap material 24' is flat and unfolded, and the tab portion 54 is facing inwardly relative to the machine direction centerline, MD (that is, in the direction of the other web of flap material). The continuous portion 56 of the web of flap material 24' is held on the first fold conveyor 86, such as by vacuum pressure, while the web of flap material 24' moves into the first folding plow 88. The first folding plow 88 folds the tab portion 54 of the web of flap material 24' along the first fold line $F_1$ over part of the rest of the web of flap material 24'. After folding, the tab portion 54 faces outwardly relative to the machine direction centerline, MD.

Figure 7A:
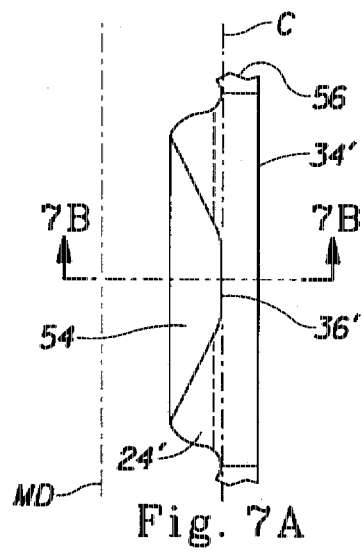
FIG. 7A is a top plan view of a section of a continuous web of flap material after it has been folded once.
Figure 7B:
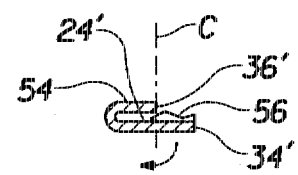
FIG. 7B is a cross-sectional view of the web of material shown in FIG. 7A taken along line 7B—7B of FIG. 7A.

FIGS. 7A and 7B show the position of the web of flap material 24' after the tab portion 54 has been folded by the first folding plow. This places the flap adhesive 48 over the unitary release material 50 (which have been omitted from FIGS. 6A to 8B for simplicity). The tab portion 54 of the web of flap material 24' is then held on the second fold conveyor 90, preferably also by vacuum pressure, while the web of flap material 24' moves into the second folding plow 92.

Figure 8A:
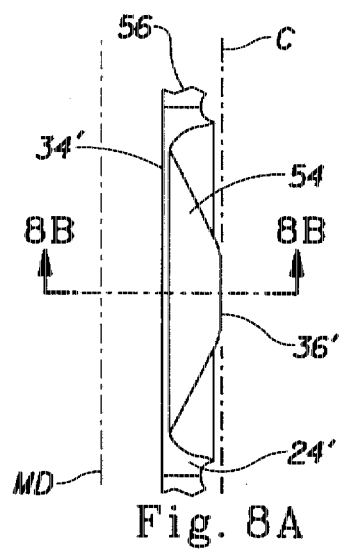
FIG. 8A is a top plan view of a section of a continuous web of flap material after it has been folded twice.
Figure 8B:
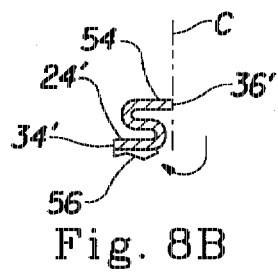
FIG. 8B is a cross-sectional view of the web of material shown in FIG. 8A taken along line 8B—8B of FIG. 8A.

FIGS. 8A and 8B show how the second folding plow 92 folds the continuous portion 56 of the web of flap material 24' along the second pre-formed fold line $F_2$ under a portion of the web of flap material that was folded in the preceding step. The tab portion 54 remains facing outwardly relative to the machine direction centerline, MD. Thus, at this stage of the folding process of the present invention, unlike prior folding processes, the discontinuous portion (or tab portion) 54 defined by the distal edge 36' of the web of flap material 24' is preferably held in position relative to the machine direction centerline, MD, and the continuous portion (or continuous ribbon) 56 of the web of flap material 24' is folded. Conventional means, such as vacuum conveyors, can hold the tab portion 54 in place while the continuous ribbon travels through the second folding plow 92 in order to fold the web of flap material 24' in the desired manner.

As shown in FIG. 4, after the folding operation, the folded webs of flap material 24' are preferably passed through the nip 66 between the pair of rollers 62 and 64. Preferably, roller 62 also serves as a drive roll for the second fold conveyor 90. The nip 66 will compress the folds into the webs of flap material 24'. After passing through the nip 66, the fold in the folded webs of flap material 24' will likely open slightly even though the folds are compressed into the webs of flap material 24'. As will be explained in greater detail below, it is acceptable, and even desirable for this to occur so that the folded flap material can have its fold adjusted and aligned about the pre-formed fold lines in the event that one or more folds are not made exactly on the pre-formed fold lines.

The folded webs of flap material 24' then preferably pass through an electrostatic charging device 68. The electrostatic charging device 68 is used to maintain the folded webs of flap material 24' in their folded configuration until they are cut into individual flaps, joined to the main body portion of the sanitary napkin, and the sanitary napkin is packaged. The electrostatic charge maintains the webs of flap material 24' in a folded configuration better than merely compressing the webs of flap material 24'. It has also been found that the electrostatic charging operation has a number of other advantages which are described below.

The electrostatic charging device 68 can comprise any suitable apparatus for imparting a static electrical charge to one side of a folded web and the opposite charge to the other side of the folded web. In the preferred embodiment of the method of the present invention, the electrostatic charging device 68 comprises a pair of cylindrical CHARGEMASTER® TETRA ™ RC-3 electrostatic generating charging bars for each of the webs (one set of which is shown as the elements designated by reference number 72) and a CH50 DC CHARGEMASTER electrostatic generating equipment power supply, obtained from the SIMCO Company, Inc. of Hatfield, Pa., a subsidiary of Illinois Tool Works Company of Glenview, Ill., or equivalent. The cylindrical charging bars 72 may be oriented in the cross-machine (CD) direction as shown in FIG. 4, or they may be turned so that their longitudinal axes are oriented in the machine direction. Preferably, the charging bars are oriented in the cross-machine direction to conserve space in the area where the manufacturing line is located.

The electrostatic charging device 68, as described above, places opposite static electrical charges on the folded webs of flap material 24'. In the preferred embodiment of the process shown where each web of flap material is folded twice, the charges will be required to penetrate three layers of material. These charges attract the layers of film to each other resulting in a tight fold that remains folded during the manufacturing process. Because polyethylene is a good insulator, the charges will remain for about a week if not disturbed.

The static charge maintains the flaps in their folded configuration until they are cut into individual flaps and joined to the main portion of the sanitary napkin. It has also been found that if the fold did not align with the pre-formed folding lines, since the electrostatic charging equipment does not produce as great of a perpendicular (or normal) force the web material as a highly compressed fold, the folded sections of the web are free to move in the cross-machine direction or shift laterally. This tends to correct any misalignment of the folds because the web inherently tends to fold along the score lines. Thus, the use of a static charge provides the ability to initially impart a less precise and uncompressed (or loose) fold and thereafter correct the same using the static charging equipment.

The static charging operation is described in greater detail in U.S. patent application Ser. No. 08/620,517 entitled "Method of Folding and Using Static Charge to Align and Retain Folded Material" (serial number to be filled in after one is assigned) filed in the name of Stoyan Lokar, et al. on the same date as the present application.

Figure 9:
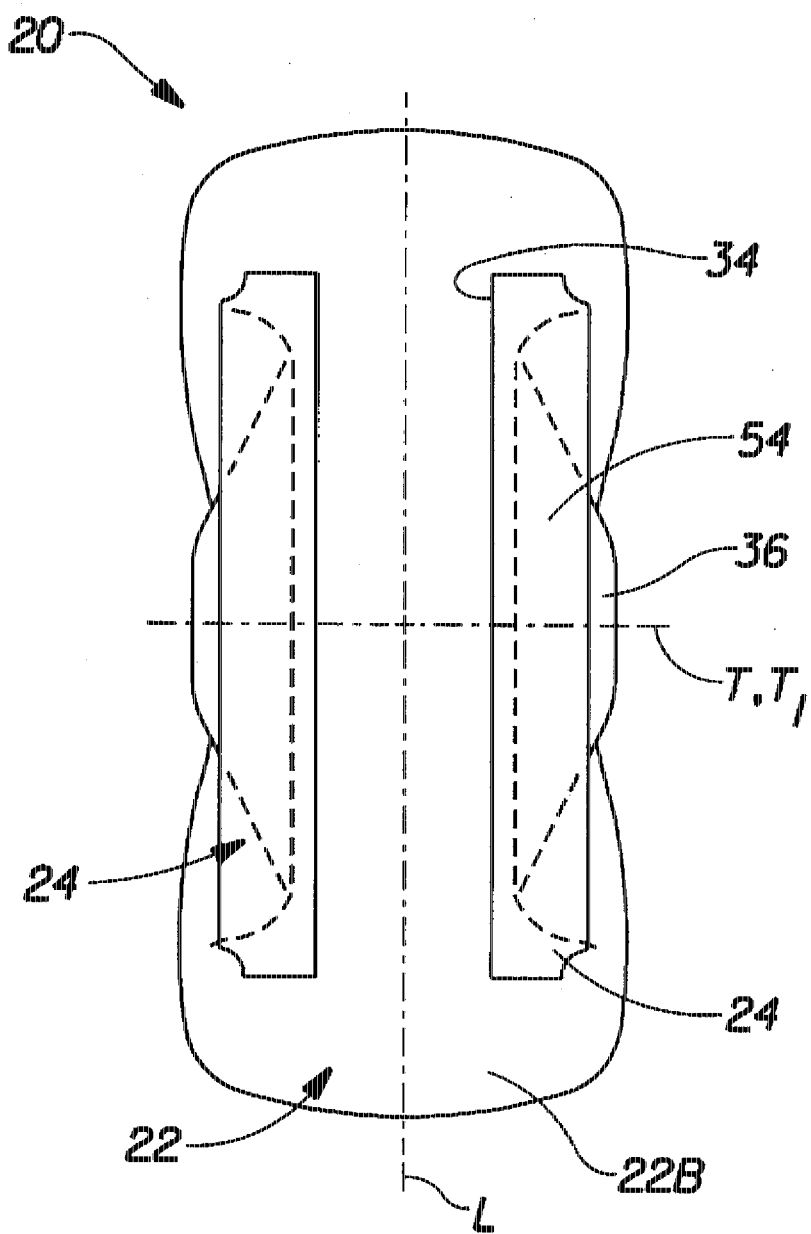
FIG. 9 is a bottom plan view of a sanitary napkin made according to the method of the present invention, shown after the webs of flap material have been folded and cut into individual flaps and attached to the garment-facing side of the main body portion.

After the static charging operation, the path of one of the folded webs 24' is preferably adjusted so that the flap transverse centerlines $T_1$ of the two webs of flap material 24' (shown in FIG. 3) are aligned. The webs of the flap material 24' then move to a continuous cutting and fastening operation where a series of main body portions are being continuously fed into the process. The webs of flap material 24' are coated with adhesive along the proximal edges 34' thereof, cut into individual flaps 24, and attached to the garment side 22B of a main body portion 22 as shown in FIG. 9. The central pad adhesive 46 is then applied to form the finished sanitary napkin 20.

The advantage of the folding process of the present invention is that it can be used to attach the folded flaps to the desired side of the main body portion of the sanitary napkin without making the webs of flap material cross over each other in order to have the tab portions extending from the correct side of the sanitary napkin. The folding process of the present invention provides the additional advantage that it is possible to fold a web and fix its orientation at the same time (instead of in separate steps as was customarily required in the past). The folding process of the present invention also provides the ability to fold and reorient a web while maintaining tight tracking tolerances previously not thought to be possible.

Many variations of the method of the present invention are possible. The step of the method of the present invention which involves holding a discontinuous portion of a web of material in position while folding a continuous portion relative thereto can be used whenever it is desirable for reorienting webs or parts of products during manufacturing process. This feature of the present method can also be used when reorienting webs or parts of products during packaging processes.

In addition to sanitary napkins, other types of absorbent articles could be provided with flaps that are folded by the method of the present invention. Suitable absorbent articles in the form of pantiliners are disclosed in U.S. Pat. No. 4,738,676 entitled "Pantiliner" issued to Osborn on Apr. 19, 1988. Such pantiliners would be provided with flaps having the configurations described herein. Suitable absorbent articles, at least some of which are in the form of adult incontinence products that could be provided with flaps that are folded by the method of the present invention, are described in U.S. Pat. Nos. 5,300,054 issued to Feist, et al. on Apr. 5, 1994, and 5,304,161 issued to Noel, et al. on Apr. 19, 1994.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A method of folding a web of flap material in a continuous manufacturing operation for making absorbent articles, wherein said web of flap material has a continuous portion and a discontinuous portion, said method comprising the steps of:

(a) providing a first web of flap material and a second web of flap material wherein each of said webs has a continuous ribbon portion and a discontinuous tab portion;

(b) transporting each of said webs of material in a machine direction wherein each of said webs of material is generally centered from lateral displacement about a centerline;

(c) maintaining the discontinuous tab portion of each of said webs of material in position relative to said centerline;

(d) folding said continuous ribbon portion of each of said webs of material about said discontinuous tab portion;

(e) cutting each of said webs of flap material into individual flaps in a continuous operation;

(f) providing a main body portion for an absorbent article; and (g) attaching one of said individual flaps to each side of said main body portion to form an absorbent article wherein one of said individual flaps was originally part of said first web of flap material and the other of said individual flaps was originally part of said second web of flap material and wherein said attachment is accomplished without having to cross said individual flaps over each other or over said main body portion.

2. A method of folding and attaching material for flaps to an absorbent article in a continuous manufacturing operation for making absorbent articles having folded and tucked flaps, wherein said flap material has a continuous ribbon portion and a discontinuous tab portion, said method comprising the steps of:

(a) providing a single continuous web of flap material;

(b) forming pre-formed folding lines into said single continuous web of flap material;

(c) cutting said continuous web of flap material into a first continuous web of flap material and a second continuous web of flap material so that said two continuous webs each have a continuous ribbon portion and discontinuous tab portions wherein said discontinuous tab portions of said two webs point toward each other;

(d) transporting each of said webs of flap material in a machine direction wherein said webs of flap material are generally centered from lateral displacement about a centerline;

(e) maintaining said continuous ribbon portions of said webs of flap material in position relative to said centerline;

(f) folding at least a portion of said tab portions of said web material over at least a portion of said flap material, to provide a first fold;

(g) maintaining the discontinuous tab portion of said web of flap material in position relative to said centerline;

(h) folding said continuous ribbon portion under said discontinuous tab portion to provide a second fold;

(i) cutting each of said two webs of flap material into individual flaps;

(j) providing a continuous supply of main body portions for an absorbent article and transporting said main body portions in a machine direction; and (k) attaching one of said individual flaps to each side of each of said main body portions to form an absorbent article having folded and tucked flaps wherein said first of said individual flaps was cut from said first web of flap material and said second of said individual flaps was cut from said second web of flap material and wherein said attachment is accomplished without having to cross said individual flaps over each other or over said main body portion.

\* \* \* \* \*

UNITED STATES PATENT AND TRADEMARK OFFICE
CERTIFICATE OF CORRECTION

PATENT NO. : 5,714,027
DATED : February 3, 1998
INVENTOR(S) : Stewart L. Taub

It is certified that error appears in the above-identified patent and that said Letters Patent is hereby corrected as shown below:

Column 9, line 50-51    after "Material" and before "filed" delete –(serial number to be filled in after one is assigned)--

Signed and Sealed this

Twenty-fifth Day of May, 1999

Attest:

Q. TODD DICKINSON

Attesting Officer    *Acting Commissioner of Patents and Trademarks*